United States Patent [19]

Lawrence

[11] Patent Number: 4,615,982
[45] Date of Patent: Oct. 7, 1986

[54] FECAL OCCULT BLOOD TEST

[76] Inventor: Paul J. Lawrence, 2082 Abbey La., Campbell, Calif. 95008

[21] Appl. No.: 680,357

[22] Filed: Dec. 11, 1984

[51] Int. Cl.$^4$ ...................... G01N 21/78; G01N 33/72
[52] U.S. Cl. ........................................ 436/66; 422/56; 436/904
[58] Field of Search ............... 422/56, 57, 58; 436/66, 436/904; 435/28

[56] References Cited

U.S. PATENT DOCUMENTS

| | | |
|---|---|---|
| 3,252,762 | 5/1966 | Adams et al. |
| 3,917,452 | 11/1975 | Rittersdorf et al. ................... 436/66 |
| 3,996,006 | 12/1976 | Pagano ............................. 422/58 X |
| 4,035,150 | 7/1977 | Jaffe . |
| 4,071,317 | 1/1978 | Lam . |
| 4,219,336 | 8/1980 | Gutbleim et al. |
| 4,251,222 | 2/1981 | White .................................... 436/66 |
| 4,251,223 | 2/1981 | White .................................... 436/66 |
| 4,260,393 | 4/1981 | Gibson . |
| 4,278,439 | 7/1981 | White .................................... 436/66 |
| 4,333,734 | 6/1982 | Fleisher . |
| 4,378,971 | 4/1983 | Schwarz . |

OTHER PUBLICATIONS

*Acta Biol Med Ger* (1975) 34:319–324.
*Biochem J* (1970) 117:741–744.
*Biochem J* (1973) 135:353–359.
*Biochem J* (1976) 153:279–285.
*Biochemistry* (1974) 13:4279–4284.
*Biochem J* (1979) 179:281–289.
*Biochem J* (1968) 108:131–136.
*Biochimica et Biophysica Acta* (1977) 498:205–214.
*Biochem J* (1979) 179:273–280.

*Primary Examiner*—Arnold Turk
*Attorney, Agent, or Firm*—Ciotti & Murashige

[57] ABSTRACT

Fecal occult blood tests of enhanced sensitivity and specificity are provided by employing (1) a developer composition comprising a solution of a hydroperoxide in a solvent comprising at least about 50% by volume of a solvent for iron protoporphyrins such as dimethyl sulfoxide and/or (2) a solid test matrix comprising a solid support impregnated with a leuco dye and a hemoprotein solubilizing agent. Test results may be further improved by incorporating plant peroxidase inhibitors, iron/copper chelating agents and buffers in the developer and/or test matrix.

13 Claims, No Drawings

FECAL OCCULT BLOOD TEST

DESCRIPTION

1. Technical Field

This invention is in the field of fecal occult blood tests (FOBT). More particularly it relates to improved FOBT that provide a reduced incidence of false results and/or greater sensitivity and specificity.

2. Background Art

FOBT are commonly used clinically to detect occult blood loss from gastrointestinal (GI) lesions. For example, carcinoma of the colon and rectum is the most serious cancer in the U.S. and second only to lung cancer in causing death—approximately 100,000 new cases and 50,000 deaths annually. Because colorectal cancer is slowly progressive with a long asymptomatic period, it provides an ideal opportunity for early detection and successful therapy. Thus, FOBT are a rational attempt at early diagnosis because the colorectal lesions frequently bleed, and routine noninvasive testing is possible. Similarly, hospitals and physicians very often utilize FOBT to detect or monitor GI lesions resulting from disease, injury, surgery, and other causes.

Early FOBT involved shipping entire 24-48 hour fecal collections in paint cans to central laboratories for testing with an acidified guaiac solution and hydrogen peroxide. Guaiac is a complex plant extract containing the leuco dye, alpha guaiaconic acid. Leuco dyes are oxidized by hydroperoxides in the presence of catalyst to form a blue color:

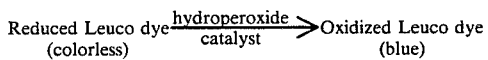

Because hemoglobin is an efficient catalyst (pseudoperoxidase), feces may be tested for occult blood using a leuco dye/hydroperoxide reagent. Nonetheless, the procedure remained very poorly utilized because of the disagreeable nature of the test and physicians were largely denied this very useful information.

U.S. Pat. No. 3,996,006 describes a FOBT technique that popularized the guaiac-based test for occult blood in feces. It employs a slide having a sheet of guaiac-impregnated paper between a front panel and a rear panel with openings in the panels and pivotal flaps to cover the openings. A fecal specimen is placed on the paper through the opening in the front panel and that panel is closed. The rear panel is then opened and a hydrogen peroxide developer is placed on the paper via the opening in the rear panel. If blood is present in the specimen, the paper will turn blue. A commercial embodiment of this test, called the HEMOCCULT ® test, is widely used in hospitals and physicians' offices. Despite the widespread popularity of the HEMOCCULT ® test recent studies have pointed out serious limitations in its sensitivity and specificity. Applicant believes that the sensitivity limitation is due partly to (1) the fact that hemoglobin in many specimens is degraded to hemoproteins that exhibit little or no peroxidative activity, (2) degradation of peroxidatively active hemoproteins by the hydroperoxide reagent used in the test and (3) relative insolubility of the degraded products (i.e., iron protoporphyrins such as heme and hemin) in the reagents used in the test. Sensitivity limitations, of course, may cause false negative results. The specificity limitation is probably due to the response of the test to plant peroxidases and/or iron or copper in the specimens or the environment in which the test is run. Specificity limitations lead to false positive results.

U.S. Pat. No. 4,333,734 describes a variation in the guaiac-based FOBT that is intended to reduce the incidence of false positive results due to the presence of plant peroxidases in the specimen. It includes a peroxidase denaturing agent such as urea or guanidine hydrochloride together with a metal chelating agent to sequester calcium and magnesium ions that are essential to peroxidase activity. The denaturant and the chelating agent are formulated with the guaiac.

U.S. Pat. No. 4,071,317 relates to using polar solvents such as dimethyl sulfoxide (DMSO) and dimethyl formamide (DMF) to stabilize mixtures of organic hydroperoxides and leuco dyes that are used in FOBT. The solvent is formulated in minor proportions with the hydroperoxide and leuco dye. This solution is applied to a solid matrix and the matrix is dried.

Several references indicate that monomeric species of iron protoporphyrins exhibit greater peroxidase activity than dimeric or aggregated species. *Biochem J* (1970) 117: 741–744; *Biochem J* (1973) 135: 353–359; *Biochem J* (1976) 153: 279–285; and *Biochemistry* (1974) 13: 4279–4284. *Biochem J* (1979) 179: 281–289 indicates that hemin occurs in its monomeric form in mixtures of DMSO and water that contain in excess of about 35% (v/v) DMSO.

*Biochem J* (1968) 108: 131–136 discusses the solubility of nitrogenous ligand-alkaline hematin complexes. *Biochimica et Biophysica Acta* (1977) 498: 205–214 describes the use of various water-soluble polymers such as polyethylene oxide, polyvinyl alcohol, polyvinyl pyrrolidone, and polystyrene sulfonate to dissolve aggregates of ferroheme and protoporphyrin in alkaline aqueous media.

A principal object of the present invention is to reduce the incidence of incorrect results (both false positive and false negative) in leuco dye-based FOBT. This is achieved by using reagents in the leuco dye-containing matrix and/or the developer that solubilize relatively insoluble hemoproteins present in the specimen and maintain them in monomeric form. In addition, reagents may be used that do not result in the degradation of peroxidatively active hemoproteins and inhibit plant peroxidase activity.

DISCLOSURE OF THE INVENTION

One aspect of the invention is a FOBT developer composition for use in FOBT using a leuco dye as an indicator comprising a solution of a hydroperoxide in a solvent comprising at least about 50% by volume of a solvent for iron protoporphyrins.

Another aspect of the invention is a solid test matrix for use in FOBT comprising a solid support impregnated with a leuco dye and a hemoprotein solubilizing agent.

Still other aspects of the invention are FOBT methods that employ either or both of the above described developer composition and test matrix.

MODES FOR CARRYING OUT THE INVENTION

As used herein the term "hemoprotein" is intended to include hemoglobin and derivatives of hemoglobin such as heme and hemin that have the ability (particularly in their monomeric form) to catalyze the transfer of oxygen from a hydroperoxide to a leuco dye to cause the leuco dye to be oxidized and thereby produce a detectable response. Such ability is sometimes referred to herein as "peroxidative activity".

The test matrices of the present invention comprise a solid support on which the leuco dye and hemoprotein solubilizing agent are impregnated. The solid support must be capable of carrying the leuco dye and solubilizing agent and being wetted by the developer composition. It may be made from a variety of porous materials such as cellulosics (wood, paper), ceramic, glass fibers, natural or synthetic cloth fibers, felt, and sponge. Bibulous filter paper is commonly used and is preferred.

As used herein the term "leuco dye" is not intended to be limited to a particular chemical species or genus but is intended to encompass indicators that produce a detectable response, typically a color change that is visible to the naked eye, when oxidized in the presence of a hemoprotein. Examples of leuco dyes are guaiac, benzidine, o-tolidine, cresol, catechol, 3,3',5,5'-tetramethylbenzidine, p-tolidine, betanaphthol, pyrogallol, o-phenylenediamine, leuco malachite green, 3-amino ethylcarbazole, 7-amino antipyrine, and 2,2'-azino-di-(3-ethylbenzyl)azoline sulfonic acid (ABTS). Guaiac is commonly used and is preferred.

Hemoprotein solubilizing agents that may be incorporated into the test matrix include detergents and water-soluble polymers. Detergents that have suitable hydrophilic-hydrophobic balance to solubilize hemoproteins are suitable. Such detergents include the Triton ® detergents (polyoxyethylene alkylphenols), detergents from the series alkyltrimethylammonium bromides, like cetyl alkyltrimethylammonium bromide (CTAB) or p-toluene sulfonic acid salts of alkyl-trimethylammonium bromide detergents, and $C_{10}$ to $C_{14}$ alkali metal salts of fatty acids or alkali metal alkyl sulfates. Examples of suitable detergents are sodium dodecyl sulfate (SDS), sodium dodecyl sulfonate, sodium decyl sulfate, sodium tetradecyl sulfate, sodium tridecyl sulfonate, sodium myristate, sodium caprate, sodium dodecyl N-sarcosinate, and sodium tetradecyl N-sacrosinate. The water-soluble polymers that may be used to solubilize hemoproteins include poly(ethylene oxide), poly(vinyl alcohol), poly(vinyl pyrrolidone), and poly(styrene sulfonate). These solubilizing agents not only solubilize hemoproteins, but are believed to convert peroxidatively inactive hemoprotien dimers or aggregates into peroxidatively active monomeric species. It is desirable to incorporate a minor proportion of a nonvolatile hemoprotein solvent such as DMSO, DMF or pyridine into the matrix along with the solubilizing agent. Incorporation of such solvents facilitates the diffusion of iron protoporphyrins in the fecal specimen into the matrix.

Nitrogenous ligands that stabilize iron protoporphyrins and enhance their peroxidative activity may also be incorporated in the test matrix. Examples of such ligands are pyridine, histidine, chloroquine, caffeine, imidazole, and imidazole derivatives.

In addition to the leuco dye and the hemoprotein solubilizing agent(s), other additives such as vegetable peroxidase inhibitors and iron chelators (e.g., ethylenediamine tetraacetic acid, citric acid, tartaric acid, nitrilotriacetic acid, diethylenetriaminepentaacetic acid, N,N¹-bishydroxyethyl glycine, ethyleneglycol bis(2-aminoethylether)tetraacetic acid, N-hydroxyethylethylenediaminetetraacetic acid) may be incorporated into the test matrix to further reduce the likelihood of false test results. Buffers may be included in the test matrix to maintain a suitable pH range for oxidizing the leuco dye. The particular buffer (pH range) will depend on the leuco dye that is used. The pH will usually be between about 3 and about 9. By way of example, guaiac oxidation is buffered at pH 6–7.5 (phosphate buffer), 3,3',5,5'-tetramethylbenzidine oxidation is buffered at a pH of about 4 (acetate buffer), and ABTS is buffered at a pH of about 9–9.5 (glycine buffer).

The impregnation of the solid support with the leuco dye, solubilizing agent, and other additives is normally carried out by dissolving the materials to be incorporated in suitable solvents, applying the solutions to the solid support, and then drying the treated support so as to leave a suitable residue of the materials on the support. The amounts of materials remaining on the support will usually be as follows:

Leuco dye (1–100 $\mu g/cm^2$);
Detergent/polymer (0.002–0.2 $\mu g/cm^2$);
Nitrogenous ligands (0.002–0.2 $\mu g/cm^2$);
Buffer (10–150 $\mu g/cm^2$);
Solvent (0.1–2.0 $mg/cm^2$); and
Chelators (0.002–0.2 $\mu g/cm^2$).

The developer composition of the invention comprises a solution of a hydroperoxide in a solvent for iron protoporphyrins. Hydrogen peroxide or organic hydroperoxides such as cumene hydroperoxide, t-butyl hydroperoxide, diisopropylbenzene hydroperoxide, and 2,5-dimethylhexane hydroperoxide may be used. It is preferred to use an organic hydroperoxide since organic hydroperoxides are less likely to (a) produce false positive results in FOBT in which vegetable peroxidases are present in the fecal specimen and (b) destroy the peroxidase activity of the hemoprotein. The concentration of hydroperoxide in the solution will usually be in the range of 0.05 to 10% by volume, more usually 0.5 to 5% by volume. Cosolvents such as water, alkanols (e.g., methanol, ethanol and other lower alkanols), pentane, ethylacetate, cyclohexane, and acetone may be included with the iron protoporphyrin solvent, but the proportion of principal solvent in the solvent composition should be maintained above about 50% (v/v), preferably above about 75% (v/v).

The use of DMSO as the solvent in the developer provides several advantages. Firstly, it is an excellent solvent for hemoproteins. Secondly, it converts heme and hemin dimers and aggregates into their monomeric forms. And, thirdly, it inactivates peroxidases that may be present in the fecal specimen and inhibits them from catalyzing the oxidation of the indicator and producing a false positive result.

The pH of the developer composition will normally be in the range of about 3 to 9, preferably 4.5 to 7.

The developer composition may also contain hemoprotein solubilizng agents such as those described above, nitrogenous ligands such as those described above, peroxidase inhibitors such as those described above, iron/copper chelating agents such as those described above, and buffers to maintain the pH of the composition and the pH at which the development occurs.

The test matrices and developer composition of the invention may be employed to detect blood in fecal specimens or samples of other body fluids using conventional procedures. The developer composition may, of course, be employed in "wet" tests (i.e., tests done in solution or suspension) for blood as well as in solid phase tests with the invention test matrix or prior matrices. In solid phase tests the specimen to be tested is placed on the test matrix. The configuration of the test matrix may be similar to the HEMOCCULT ® matrix such that both sides of the matrix are accessible so that the specimen can be applied to one side and the developer to the other. The developer solution is then placed on the matrix. Because the matrix and the developer contain materials that solubilize hemoproteins is it not essential that the developer be applied directly onto the spot at which the specimen was applied. The solubilizers will cause hemoproteins to be dissolved and carried by the solent to the area of the matrix wet by the solvent. In this regard it may be desirable to apply the developer to the side of the matrix to which the specimen was applied to take advantage of the ability of the developer to dissolve hemoproteins in the specimen and transport them to the matrix where they are available to catalyze leuco dye oxidation. Such application may improve the sensitivity of the test.

The FOBT materials and procedures of the invention and their advantages over previous materials and procedures are illustrated by the following examples. These examples are not intended to limit the invention in any manner.

EXAMPLE 1

Tests were carried out to compare the specificity and sensitivity achieved in FOBT with a developer composition of the invention (5% (v/v) cumene hydroperoxide (CHP) in DMSO) versus that achieved with a conventional FOBT developer (3–6% (v/v) hydrogen peroxide in ethanol/water).

Serial dilutions of hemin (0.1 mg/ml in 1 mM ammonium hydroxide), hemoglobin (Hb, 1.0 mg/ml), and horse radish peroxidase (HRPO, 20 U/ml) in water were prepared. Two $\mu l$ of these dilutions were applied to HEMOCCULT ® slides and the spots were allowed to dry. Five $\mu l$ of developer composition was applied to each spot. After one minute the presence or absence of blue color on the slide was noted ($+++$ =intense color; $++$ =strong color; $+$ =clearly visible color; $\pm$ =barely perceptible color; $-$ =no detectable color). The results of these tests are shown in Table 1 below.

TABLE 1

| Dilution | Hemin $H_2O_2$ | Hemin CHP | Hb $H_2O_2$ | Hb CHP | HRPO $H_2O_2$ | HRPO CHP |
|---|---|---|---|---|---|---|
| 0 | +++ | +++ | +++ | +++ | +++ | ++ |
| 2 | +++ | +++ | +++ | +++ | +++ | + |
| 4 | +++ | +++ | +++ | +++ | +++ | ± |
| 8 | ++ | ++ | +++ | ++ | +++ | − |
| 16 | ± | + | + | ++ | +++ | − |
| 32 | − | ± | ± | + | ++ | − |
| 64 | − | − | ± | ± | ++ | − |
| 128 | − | − | − | ± | + | − |
| 256 | − | − | − | − | ± | − |
| 512 | − | − | − | − | ± | − |

As indicated by the results of Table 1, the invention developer was more sensitive than the conventional developer with hemoglobin and hemin and much less sensitive than the conventional developer with horseradish peroxidase. The invention developer thus improves the sensitivity and specificity of the test. Sensitivity can be improved by modifying the developer as needed.

EXAMPLE 2

Tests were carried out to determine the effect of including detergents that denature HRPO into the solid support. Aqueous SDS (5%) or Triton X-100 (2.5%) were added to HEMOCCULT ® slides (12.5 $\mu l$) and allowed to dry.

Serial dilutions of HRPO were made up as in Example 1. HEMOCCULT ® slides were spotted with the HRPO dilutions as in Example 1. Conventional developer and invention developer (1.25% CHP) were placed on these slides as in Example 1 and the slides were read as in Example 1. Table 2 reports the results of these tests.

TABLE 2

| | $H_2O_2$ Developer | | | CHP Developer | | |
|---|---|---|---|---|---|---|
| HRPO Conc (U/ml) | No Addn | SDS | Triton | No Addn | SDS | Triton |
| 20.0 | + | + | + | + | + | ± |
| 10.0 | + | + | + | + | − | − |
| 5.0 | + | + | + | + | − | − |
| 2.5 | + | + | + | ± | − | − |
| 1.25 | + | + | + | − | − | − |
| 0.625 | + | + | + | − | − | − |
| 0.312 | + | + | + | − | − | − |
| 0.155 | + | + | + | − | − | − |
| 0.078 | + | ± | ± | − | − | − |
| 0.039 | + | − | ± | − | − | − |
| 0.019 | + | − | − | − | − | − |
| 0.009 | + | − | − | − | − | − |
| 0.005 | ± | − | − | − | − | − |
| 0.002 | − | − | − | − | − | − |
| 0.001 | − | − | − | − | − | − |

The results of Table 2 show that the addition of SDS or Triton detergent to the solid support would improve the specificity of the test for both the conventional developer and the invention developer. The results also indicate that the invention developer would be more specific than the conventional developer when SDS or Triton X-100 is added to the support.

Tests were also carried out to determine the effect of detergent concentration on specificity. The tests were run as above using varying concentrations of SDS or Triton on the solid support. These tests are reported in Table 3 below (HRPO concentration, 5 U/ml).

TABLE 3

| | $H_2O_2$ | | CHP | |
|---|---|---|---|---|
| Conc (%) | SDS | Triton | SDS | Triton |
| 5.00 | − | − | − | − |
| 2.50 | − | − | − | − |
| 1.25 | − | − | − | − |
| 0.62 | − | − | − | − |
| 0.31 | − | + | − | − |
| 0.16 | + | + | − | − |
| 0.08 | + | + | − | − |
| 0.04 | + | + | − | − |
| 0.02 | + | + | + | + |
| 0.01 | + | + | + | + |

Similar results would be achieved by incorporating detergent in the developer rather than the solid support.

EXAMPLE 3

Hemin degradation tests were carried out using conventional FOBT developer and FOBT developer compositions of the present invention as follows.

Hemin was dissolved in a 1:10 (v/v) mixture of DMSO and water. Two $\mu l$ of this solution was spotted onto filter paper and the paper was air dried. Spotted areas were then treated with 5 $\mu l$ of one of the following developers: (a) CHP, 5%, in DMSO; (b) t-butyl hydroperoxide, 5%, in DMSO; (c) $H_2O_2$, 5% in water; (d) HEMOCCULT ® developer ($H_2O_2$, 5%, in ethanol/water); (e) DMSO alone; (f) water alone; and (g) 75% ethanol, 25% water. The developer-treated areas were then air dried and 10 μl of guaiac solution (30 g/1200 ml isopropanol) was applied to each spot followed by air drying. Each spot was then treated with 15 μl HEMOCCULT ® developer and color change was observed. Visible blue color was noted on each spot except those treated with (c) and (d). These results indicated that organic hydroperoxides in DMSO do not effect adversely the catalytic activity of hemin, whereas conventional FOBT developer does have an adverse effect on hemin activity in FOBT. Similar results were observed using native and denatured hemoglobin instead of hemin.

EXAMPLE 4

Tests were conducted using developer compositions consisting of CHP at 5% in DMSO with various cosolvents. The procedure of Example 1 was used except that the highest clearly detectable dilution of catalyst is noted rather than color intensity. Conventional developer and CHP in other solvents were run for comparison. The results are reported in Table 4 below.

TABLE 4

| Oxidant | Solvent | Highest Detectable Dilution | | |
|---|---|---|---|---|
| | | Hm | Hb | HRPO |
| Hydrogen Peroxide | ~75% ethanol | 5 | 5 | 10 |
| CHP | 100% DMSO | 6 | ND | 4 |
| CHP | 75% DMSO 25% Pentane | 5 | ND | 5 |
| CHP | 50% DMSO 50% Pentane | 5 | ND | 6 |
| CHP | 75% DMSO 25% ethyl acetate | 5 | ND | 5 |
| CHP | 75% DMSO 25% Cyclohexane | 5 | ND | 5 |
| CHP | 50% DMSO 50% Cyclohexane | 5 | ND | 5 |
| CHP | Dimethyl Formamide | 7 | 8 | 8 |
| CHP | Acetonitrile | 7 | ND | 9 |
| CHP | 90% DMSO 10% Acetone | 4 | 4 | 3 |
| CHP | 75% DMSO 25% Acetone | 4 | 5 | 3 |
| CHP | 50% DMSO 50% Acetone | 4 | 5 | 5 |
| CHP | 100% EtOH | 4 | 6 | 7 |
| CHP | 100% MeOH | 5 | 8 | 7 |

ND = not determined

The results of Table 4 show that CHP developer with DMSO at >50% show reduced sensitivity to HRPO while retaining sensitivity for hemin. The best results occur using DMSO at 75% and above.

EXAMPLE 5

Tests were carried out to assess the effect of the developer composition on the mobility of hemin spotted on filter paper. This is an indirect measure of the solubility of hemin in the developer.

Whatman filter paper was soaked with 10 μl of a 1 mg/ml hemin solution in 1 mM aqueous ammonium hydroxide. After drying, a small section of the hemin-treated paper was placed on a HEMOCCULT ® slide. Ten μl of developer compositions comprising 5% CHP in DMSO/water solvent containing 100%, 95%, 90%, 80%, 75%, 50%, and 25% (v/v) DMSO were placed on the hemin spots and blue color formation was observed. At DMSO concentrations above about 75% blue color was noted in the entire slide area wetted by the developer. At lower DMSO concentrations color was observed only directly under the hemin-treated filter paper. A similar test with HEMOCCULT ® developer produced no color.

Similar tests using hemoglobin instead of hemi gave similar results.

EXAMPLE 6

The effect of hemoglobin denaturation on FOBT sensitivity using the developer composition of the invention and HEMOCCULT ® developer was determined as follows.

Hemoglobin was denatured by treatment with (a) hydrochloric acid, (b) enzymes or (c) heat as follows:

(a) Acid

Dilute (0.1M) hydrochloric acid was added to a solution of hemoglobin in water (5 mg/ml) until the pH of the solution was 1.0. The solution was incubated for 1 hour at 37° C. and the pH adjusted to 7.4 with 0.1N sodium hydroxide. The resulting material was homogenized to produce a finely dispersed suspension and incubated at 37° C. for 48 hours.

(b) Enzymes

Solid trypsin (1 mg) and chymotrypsin (1 mg) were added to a solution of hemoglobin in water (5 mg/ml) and incubated for 48 hours at 37° C. The resulting mixture was homogenized to produce a smooth suspension.

(c) Heat

A solution of hemoglobin in water (5 mg/ml) was heated to 75° C. for 10 minutes and incubated at 37° C. for 48 hours. The resulting mixture was homogenized to produce a smooth suspension.

Whatman filter paper was spotted with 2 μl of an aqueous solution (5 mg/ml) of the denatured hemoglobins or native hemoglobin and allowed to dry. The spot of paper containing native or denatured hemoglobin was cut out from the filter paper sheet and place directly onto a HEMOCCULT ® slide. The slides were then treated with developer compositions consisting of 5% CHP in DMSO/water at varying DMSO concentrations. Comparison slides were treated with HEMOCCULT ® developer. Color intensities were observed as above. Table 5 reports the results of these tests. (+5=extremely intense color; +1=slight color; −=no color; ±=barely detectable; ND=not done.)

TABLE 5

| | Color Intensity | | | |
|---|---|---|---|---|
| Percent DMSO | Acid Treated Hb | Enzyme Treated Hb | Heat Treated Hb | Native Hb |
| 100 | 2 | 3 | 5 | 5 |
| 95 | 2 | 3 | 5 | 5 |
| 90 | 1 | 3 | 4 | 4 |
| 85 | 1 | 2 | 4 | 4 |
| 75 | 1 | 2 | 2 | 2 |
| 50 | 1 | 1 | ± | 3 |
| 25 | ± | ± | ND | ± |
| HEMOCCULT ® Developer | − | − | − | − |

The data reported in Table 5 indicates that the sensitivity of the FOBT using the invention developer is not affected by hemoglobin denaturation as much as FOBT using conventional developers. This is particularly significant since such denaturation is likely to occur to hemoglobin in the GI tract.

Modifications of the above described modes for carrying out the invention that are obvious to those of skill in the art of biochemistry and FOBT, in particular, are intended to be within the scope of the following claims.

I claim:

1. In a fecal occult blood test wherein a fecal specimen is placed on a solid test matrix having a leuco dye impregnated therein and a hydroperoxide developer solution is subsequently placed on the matrix, the improvement comprising applying as the hydroperoxide developer solution a solution whose solvent comprises at least 50% by volume of dimethyl sulfoxide.

2. The fecal occult blood test of claim 1 wherein the solvent includes a cosolvent selected from the group consisting of water, alkanol, pentane, ethyl acetate, cyclohexane, and acetone.

3. The fecal occult blood test of claim 1 wherein the solvent is 100% dimethyl sulfoxide.

4. The fecal occult blood test of claim 1 wherein the hydroperoxide is an organic hydroperoxide.

5. The fecal occult blood test of claim 1 wherein the hydroperoxide is cumene hydroperoxide.

6. The fecal occult blood test of claim 1 wherein the dimethyl sulfoxide comprises at least about 75% by volume of the solvent.

7. The fecal occult blood test of claim 6 wherein the solvent includes a cosolvent selected from the group consisting of water, alkanol, pentane, ethyl acetate, cyclohexane, and acetone.

8. The fecal occult blood test of claim 1 wherein the solution contains at least one additive selected from the group consisting of hemoprotein solubilizng agents, nitrogenous ligands, iron and copper chelating agents, plant peroxidase inhibitors, and buffers.

9. The fecal occult blood test of claim 8 wherein the solvent comprises at least about 75% by volume dimethyl sulfoxide and the hydroperoxide is cumene hydroperoxide.

10. The fecal occult blood test of claim 1 wherein the solid test matrix is additionally impregnated with a hemoprotein solubilizing agent.

11. The fecal occult blood test of claim 10 wherein the hemoprotein solubilizing agent is capable of converting peroxidatively inactive hemoprotein dimers or aggregates into peroxidatively active hemoprotein monomers.

12. The fecal occult blood test of claim 10 wherein the hemoprotein solubilizing agent is a Triton detergent, an alkyltrimethylammonium bromide-based detergent, alkyltrimethylammonium bromide p-toluene sulfonate detergent, a $C_{10}$ to $C_{14}$ alkali metal salt of a fatty acid, or a $C_{10}$ to $C_{14}$ alkali metal alkyl sulfate.

13. The fecal occult blood test of claim 10 wherein the hemoprotein solubilizing agent is sodium dodecyl sulfate.

* * * * *